United States Patent [19]

Morrison

[11] 4,132,229
[45] Jan. 2, 1979

[54] SAFETY BELT FOR RESTRAINING BED PATIENTS

[75] Inventor: Robert D. Morrison, Columbus, Ohio

[73] Assignee: Morrison Medical Products Company, Columbus, Ohio

[21] Appl. No.: 819,714

[22] Filed: Jul. 28, 1977

[51] Int. Cl.² ............................................. A61F 13/00
[52] U.S. Cl. .................................................. 128/134
[58] Field of Search ............................. 128/133–135; 5/335; 297/384; 2/69.5

[56] References Cited

U.S. PATENT DOCUMENTS

| 2,520,710 | 8/1950 | Brown | 128/134 |
|---|---|---|---|
| 2,917,044 | 12/1959 | Bassin | 128/134 |
| 3,108,292 | 10/1963 | Bodnar et al. | 128/134 |
| 3,182,338 | 5/1965 | Shirrod | 5/336 |
| 3,817,245 | 6/1974 | Kroeger | 128/134 |

Primary Examiner—Lawrence W. Trapp
Attorney, Agent, or Firm—Frank H. Foster

[57] ABSTRACT

A general purpose, safety belt for restraining bed patients against falling out of bed. The belt confines a patient to an arc of relatively free rolling movement within limits of a 90° roll in each direction. A pair of laterally offset, securing straps attach to the bedsides and surround the patient. A pair of upper and lower, central, cross straps transvesely intersect and are sewn at their ends to a central portion of the securing straps. A soft pad is attached above the crossed straps, quick release buckles facilitate convenient but secure attachment to the bed and a locked or more difficult to release buckle secures the belt about the patient.

7 Claims, 7 Drawing Figures

SAFETY BELT FOR RESTRAINING BED PATIENTS

BACKGROUND OF THE INVENTION

This invention relates generally to body restraints and more particularly relates to a safety roll belt which provides a safe and effective means for preventing a patient from falling out of bed while allowing the patient to have roll mobility so that the patient may sleep with comfort and security.

For decades people have, from time to time, suggested a broad variety of bed patient restraints such as the patents disclosing such structures in the U.S. Patent Office in Class 5, subclass 336 and in Class 128, subclass 134. Many of these devices, while effectively restraining a patient against falling out of bed, do so at a substantial sacrifice in patient comfort. In addition, many are a rather complicated sometimes horrifying assortment of straps and buckles which are likely to cause patient apprehension.

Some of these prior art safety belts have a noose-like arrangement and may become tightened as the patient moves to different positions. Other devices tend to bind or become tangled as a patient rolls. Still others may have their structural components become misaligned or folded and thereby create a lump or protruding edge under the patient which may not only cause discomfort but also may in fact create a pressure point and abrasion leading to skin trauma and bed sores.

OBJECTS AND SUMMARY OF THE INVENTION

It is therefore an object of the present invention to provide a safety belt in which any tension forces applied to the straps which secure the belt to the bed would not be transferred to the straps which surround the patient. Therefore a comfortable, custom fitted and non-cinching waist fit is assured for every patient while also permitting the belt to be more tightly secured to the bed.

A further object of the invention is to provide a safety belt which will not tighten around the patient's waist as he rolls over or sits up.

A further object and feature of the present invention is to provide a personal, comfortable, safety belt which allows relatively free and non-restraining patient movement within arc of at least 180° and in the sitting up attitude while positively confining the patient within these limits of freedom to prevent falling from the bed.

A still further object and feature of the invention is to provide a safety belt which can not become entangled or folded and which thereby does not cause patient discomfort or trauma.

Further objects and features of the invention will be apparent from the following specification and claims when considered in connection with the accompanying drawings illustrating several embodiments of the invention.

In summary, the invention has a pair of laterally offset, flexible securing straps and a pair of cross straps transversely intersecting intermediate portions of the securing straps and transversely crossing each other. One of the cross straps is attached at its opposite ends to two of the similarly facing sides of each securing strap and the other of the cross straps is attached at its opposite ends to the other sides of the securing straps.

Figure 1:
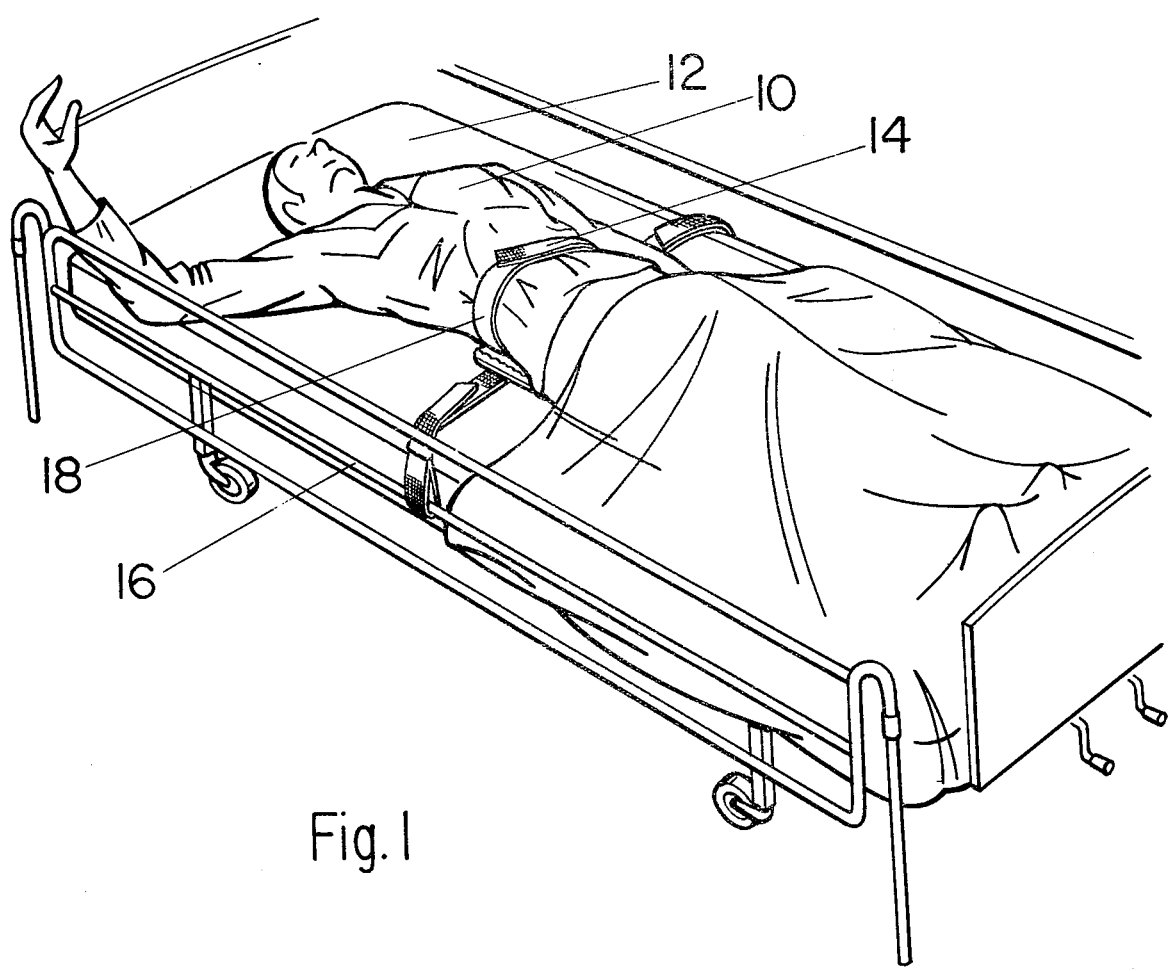
FIG. 1 is a view in perspective of an embodiment of the invention operably positioned on a bed patient.

In describing the preferred embodiment of the invention illustrated in the drawings, specific terminology will be resorted to for the sake of clarity. However, it is not intended to be limited to the specific terms so selected and it is to be understood that each specific term includes all technical equivalents which operate in a similar manner to accomplish a similar purpose.

DETAILED DESCRIPTION

FIG. 1 illustrates a patient 10 lying in a hospital bed 12 with a safety belt 14, embodying the present invention, secured to both the patient 10 and the bed 12. The safety belt is secured to the sides of the bed 12, preferably to the tie bars such as tie bar 16 which is customarily provided on hospital beds. The safety roll 14 also has a girth portion 18 which surrounds the patient.

Figure 2:
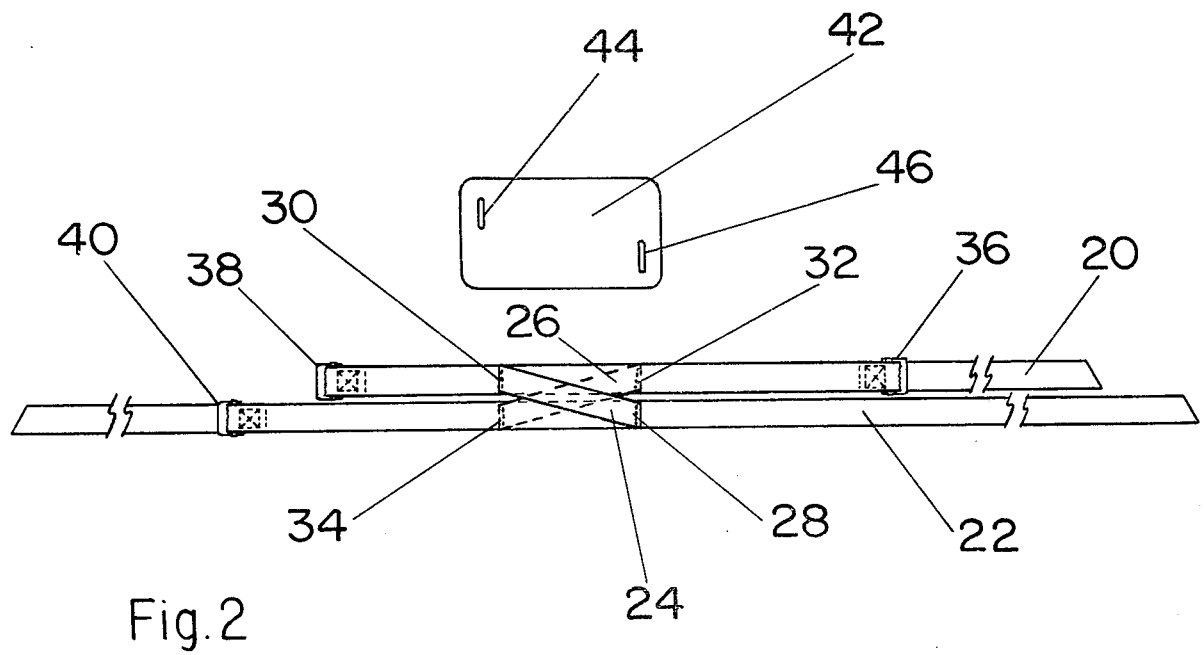
FIG. 2 is a plan view of the preferred embodiment of the invention illustrated in FIG. 1.

FIG. 2 illustrates the preferred embodiment of the invention as it would appear if supported upon a flat surface in order to illustrate its structural features of construction. The safety belt has a pair of laterally offset, flexible, securing straps 20 and 22 which, when supported on a flat surface, are generally parallel. A pair of cross straps 24 and 26 are attached to the securing straps 20 and 22 at an intermediate portion of the securing straps 20 and 22. These cross straps 24 and 26 transversely intersect or cross the securing straps and also transversely cross each other. All the straps are preferably made of the same type of heavy duty webbing.

One of the cross straps 24 is attached at its opposite ends 28 and 30 to the upper two of the similarly facing sides of each of the securing straps 20 and 22. This first cross strap 24 may be designated the upper strap as it appears on top of the securing straps 20 and 22. The other cross strap 26 is attached at its opposite ends 32 and 34 to the other or underside of the securing straps 20 and 22 and may therefore be designated as the lower cross strap. The preferred means of attachment is by sewing or stitching to form a seam near the ends of the cross straps 24 and 26.

Connector means, which are preferably quick release buckles 36 and 40, are attached to the securing straps 20 and 22, one near one end of securing strap 20 and the other near the opposite end of securing strap 22. These connector means 36 and 40 are conveniently used for securing the strap ends to which they are connected to the bed sides. It should be understood, however, that the invention contemplates the possibility that the straps may be secured to the bed by other means such as by mere tying and that consequently these connector means are not essential. They do, however, offer improved convenience and security and facilitate accurate adjustment.

A third connector means, such as the buckle 38, is connected to one of the remaining ends of the securing straps 20 and 22. As illustrated, buckle 38 is connected to one end of securing strap 20 so that the opposite end of securing strap may be secured to the buckle 38 to form the patient girth.

A soft pad 42, preferably made of Kodel, is attached to the safety belt above the upper cross strap 24. This pad is provided with slots 44 and 46 through which the girth-forming portions of the securing straps 20 and 22 extend. Therefore, the securing straps 20 and 22 extend from their regions of attachment to the upper cross strap 24 at their ends 28 and 30 through a different one of the slots in the pad 42 and into attachment with each other preferably at the buckle 38.

Referring now to FIGS. 3 through 7, the safety roll belt of the present invention may be attached to a patient so that it provides a unique, flip-flop or double axis pivot action with relatively free rolling motion within an arc of 180° but providing stops at the outer limits of this free movement arc.

The first securing strap 20 is attached near its end having the buckle 36 to the side of the bed and extends from this attachment laterally upon the bed 12, beneath the patient 10 to the opposite side of the patient so that a portion of the strap 20 at least partially surrounds the patient 10. The second securing strap 22 is attached near its end having the buckle 40 to the opposite side of the bed 12 and is laterally offset from the first securing strap 20. The strap 22 also extends from its position of attachment, laterally upon the bed 12 beneath the patient 10 to the other side of the patient so that a portion of the strap 22 at least partially surrounds the patient. The second end of the second strap 22 extends into connection with the second end of the first strap securing 20 having the buckle 38 so that the patient girth is provided.

In order to provide the desired operation so that the patient may move freely within limits but is positively stopped at the limits, the upper cross strap 24 must be attached to the securing straps 20 and 22 at regions which are nearer to the second ends or girth portion of the securing straps than the regions at which the lower cross straps are attached to the securing straps.

Figure 3:
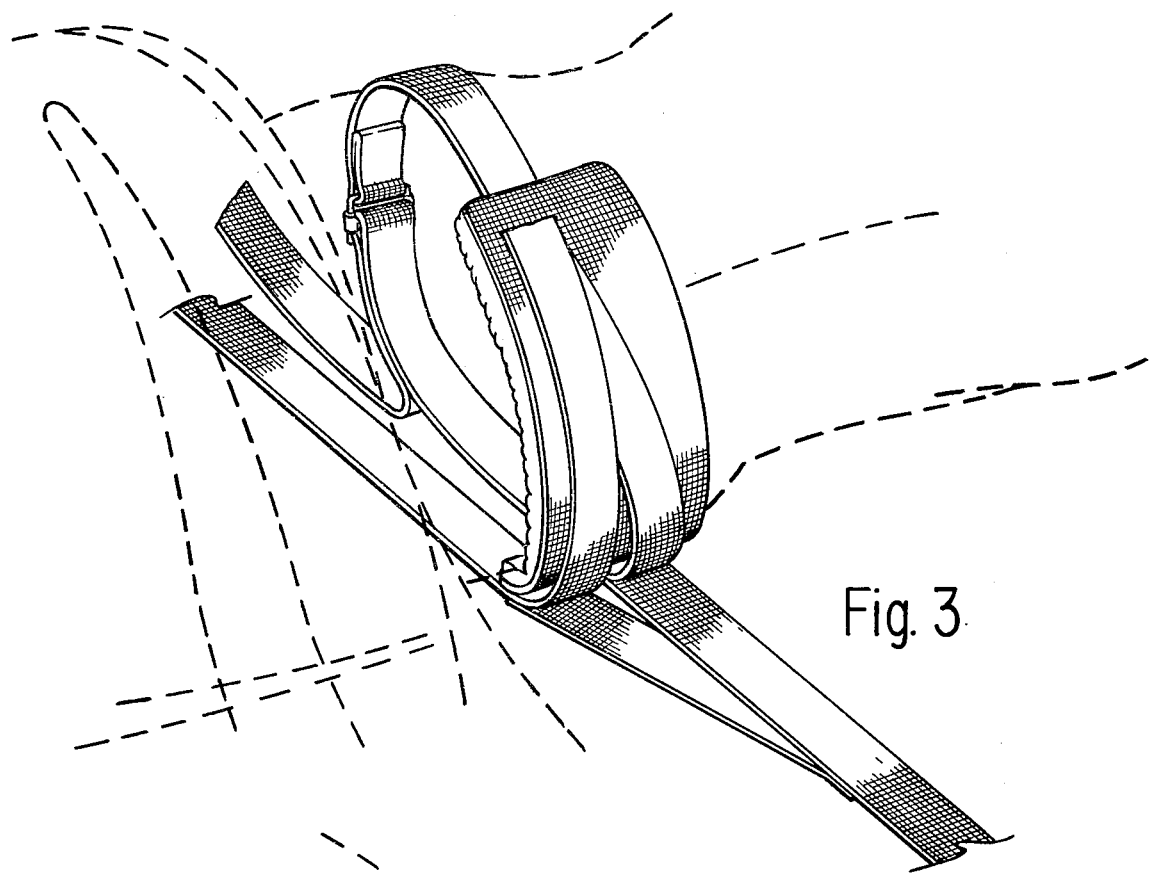
FIG. 3 is a view in perspective of a patient rolled on his side illustrating the operation of the preferred embodiment of FIG. 1.
Figure 4:
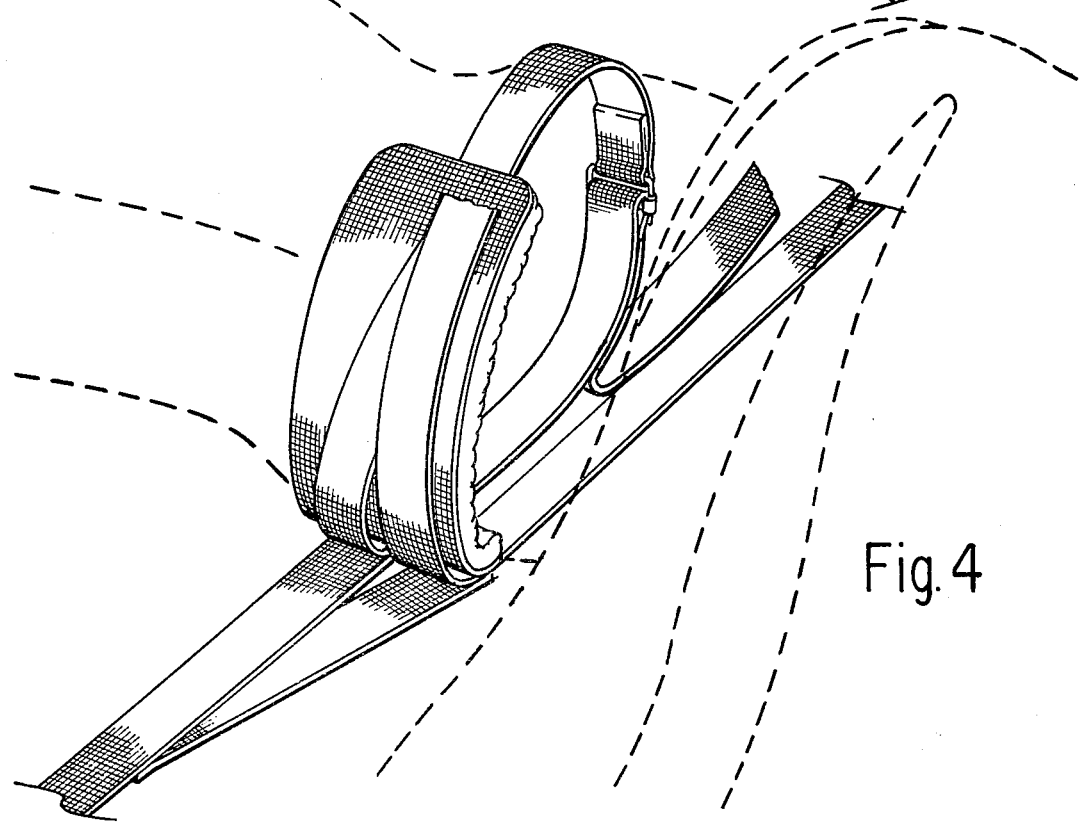
FIG. 4 is a view similar to FIG. 3 but showing the patient rolled on his opposite side.
Figure 5:
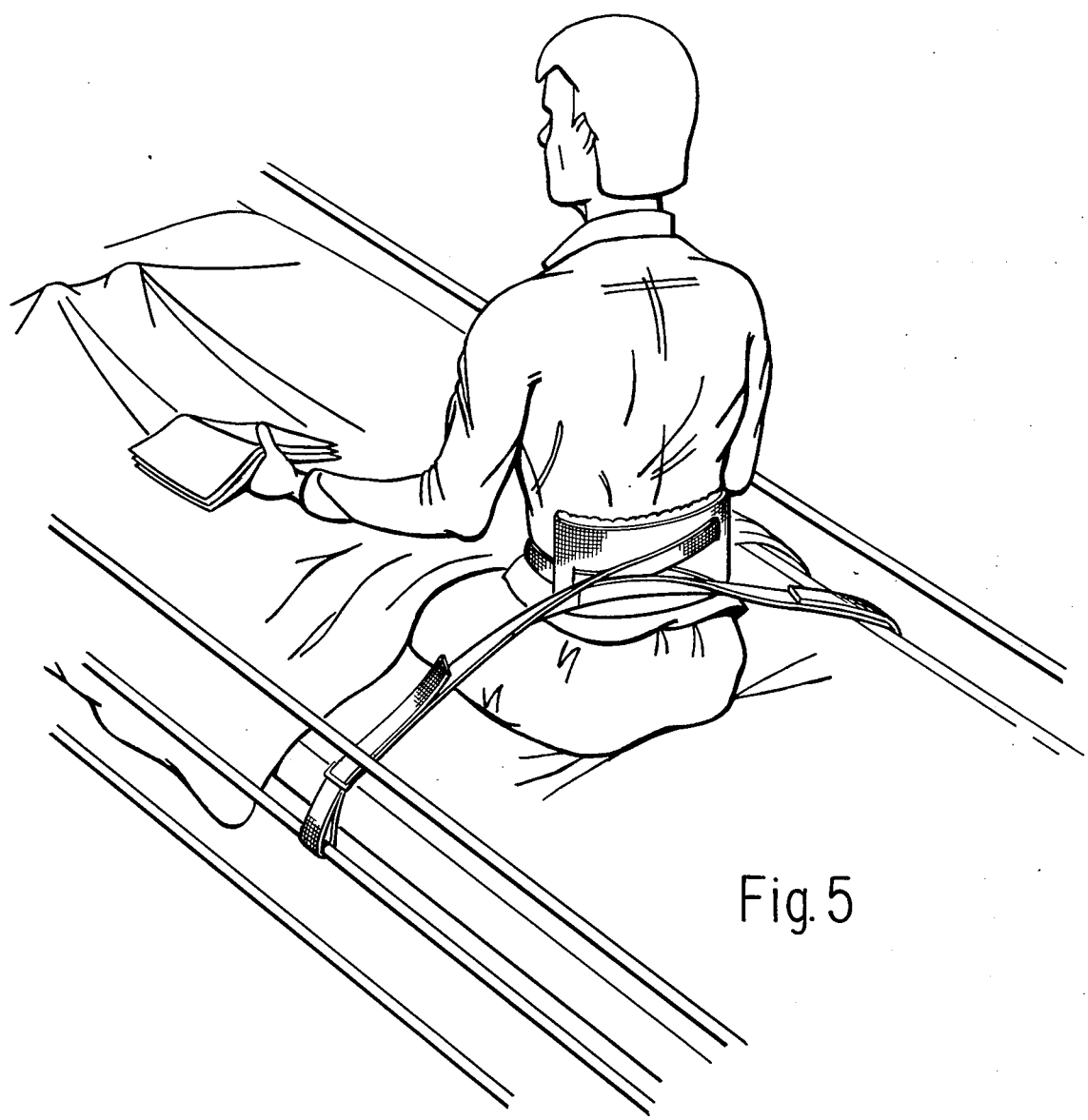
FIG. 5 is a view in perspective of the patient of FIG. 1 in the sitting position.
Figure 6:
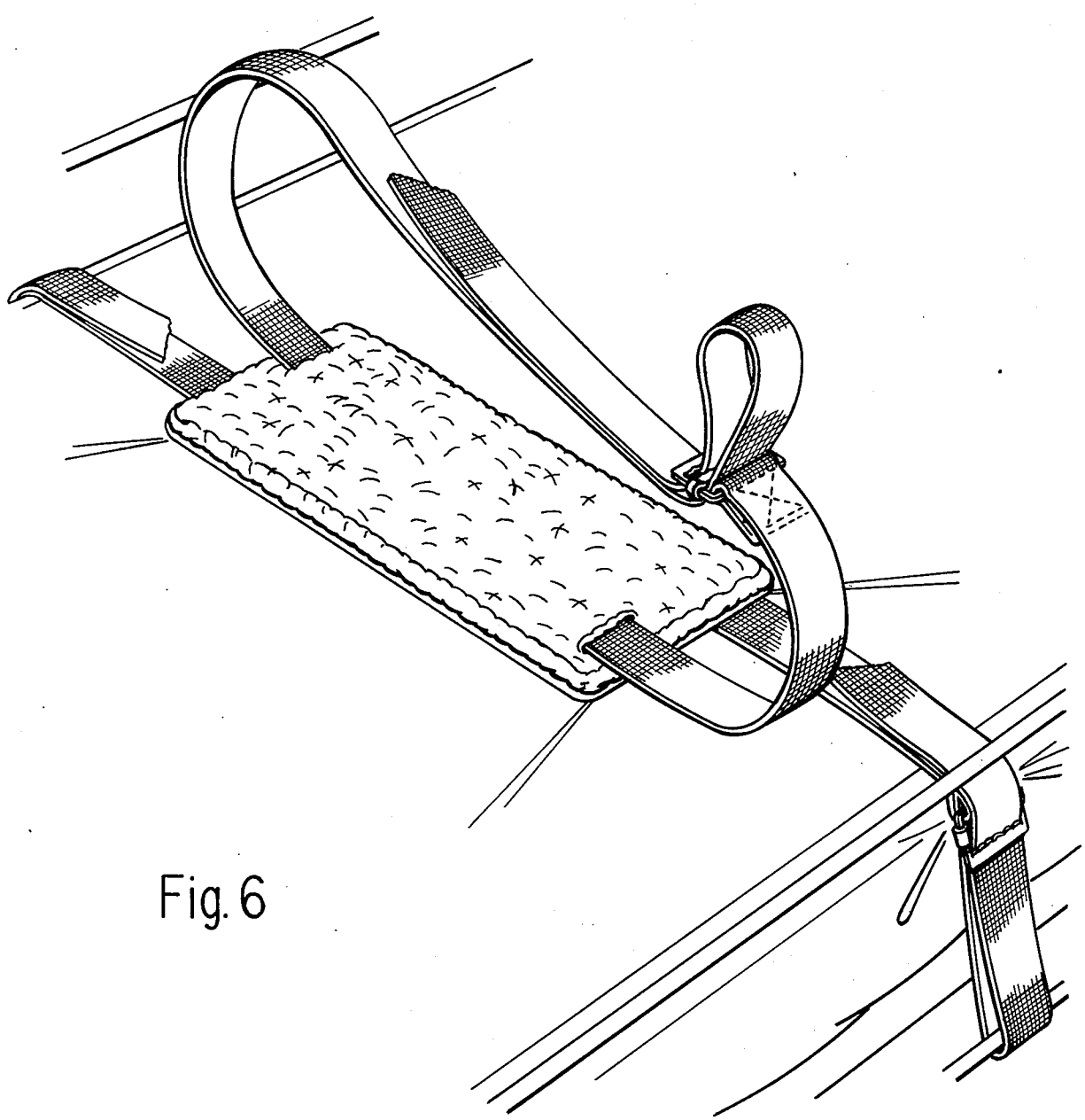
FIG. 6 is a view in perspective of the preferred embodiment with the pad properly in position.
Figure 7:
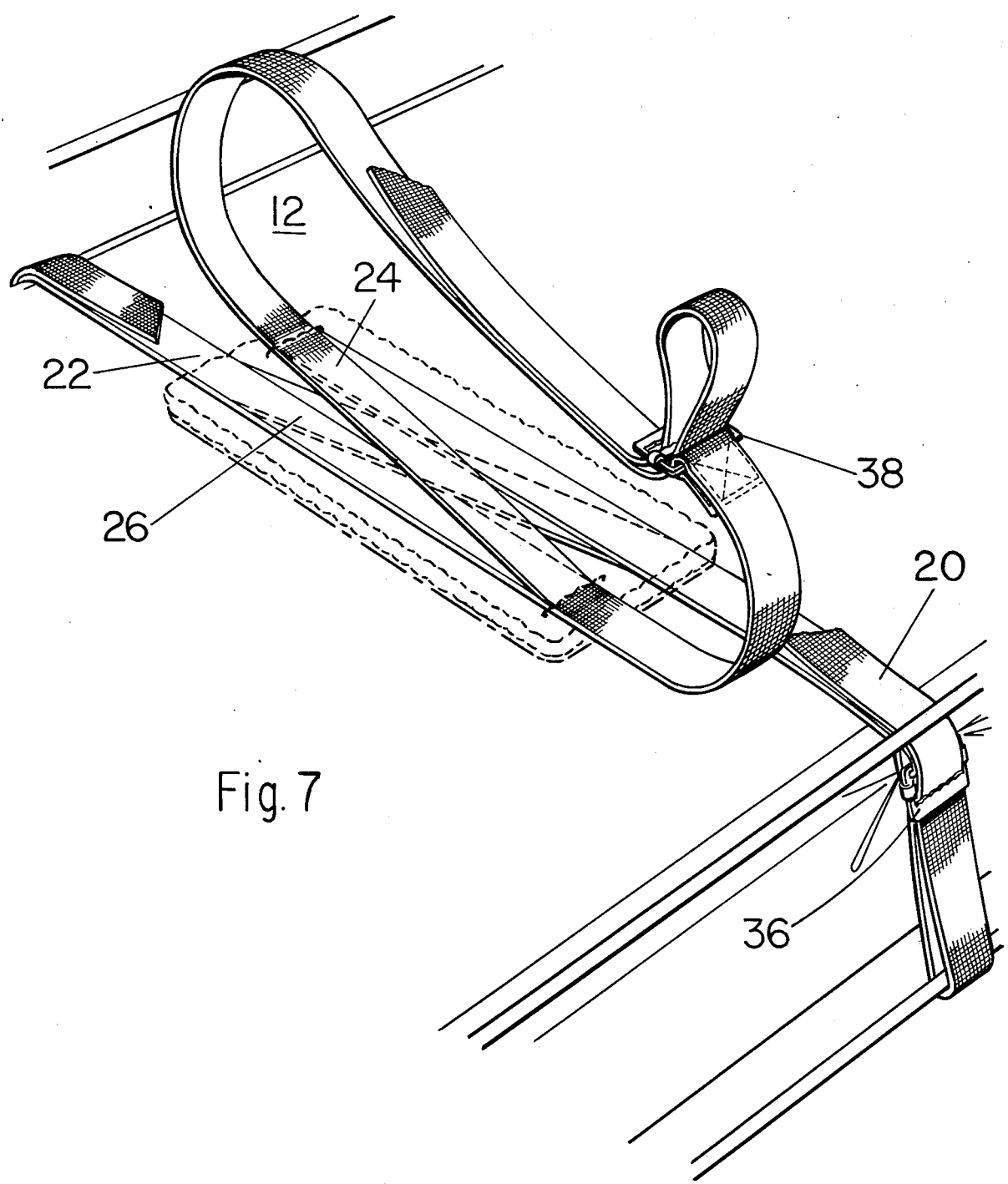
FIG. 7 is a view in perspective similar to FIG. 6 with the pad shown in phantom.

FIGS. 3, 4 and 6 illustrate the operation of the preferred embodiment of the invention. The belt provides a dual axis operation so that when the patient rolls in one direction he generally pivots about one axis and in the other direction he pivots about the other axis. The pivot axes are formed at the seams which connect the cross straps 24 and 26 to the securing straps 20 and 22.

A patient, beginning a roll from a supine position in the direction illustrated in FIG. 3, may roll about a pivot axis approximately defined by the seams at same ends of the cross straps which attach the cross straps to the securing straps. However, a roll in the opposite direction will be roughly around a pivot axis generally defined by the seams at the opposite ends of the cross straps 24 and 26.

One advantageous result of the dual pivot axis is that the embodiment of the invention also opposes misalignment or skewing of the patient on the bed and instead helps maintain the patient's body orientation parallel to the bed to a considerably greater degree than is possible with a belt with one central pivot axis.

Consequently, within the arc of relatively free movement, the pivot axes about which a person normally pivots to his side when unrestrained is almost the same pivot axes allowed by the safety roll belt of the present invention. Consequently, in rolling from the supine position to a 90° roll position or slightly further, there is no restraint upon the patient. However, if the patient attempts to roll further, for example onto the patient's stomach, the cross straps are drawn into tension to prevent such further rolling.

As the patient returns to the supine position or rolls even further in the opposite direction all of the overlying straps fall into and return to proper alignment in their original position and thereafter work similarly in the opposite direction. There is no opportunity for folding or misalignment.

The distance or spacing between the seams at the opposite ends of the cross straps 24 and 26 determines the arc of relatively free rolling movement and the position of the limits of that movement. The longer one makes the cross straps 24 and 26 and therefore the further apart the seams near their ends are sewn, the greater is the arc of relatively free rolling motion. As the seams are made closer together, the arc of relatively free motion is narrowed. Preferably the seams which define the pivot axes are formed just inside or centrally of the person's hips.

I have found that in order to confine persons who are within the usual range of human girth dimensions to slightly more than an arc of relatively free movement of 180°, the distance between the seams which attach the cross straps 24 and 26 to the securing straps 20 and 22 should be in the range of from 7 inches to 15 inches.

The length of those portions of the securing straps 20 and 22 having the buckles 36 and 40 and therefore which are intended to be secured to the bedsides is determined by the mattress width, thickness and height above the tie bar. I have found it advantageous to make each of these strap portions approximately 30 inches in length.

While embodiments of the present invention are particularly useful for hospital or other medical uses, other embodiments may be useful in other fields. For example, a belt embodying the present invention may be used as a vehicle seat belt, especially for children or for restraining animals.

It is to be understood that while the detailed drawings and specific examples given describe preferred embodiments of the invention, they are for the purpose of illustration only, that the apparatus of the invention is not limited to the precise details and conditions disclosed and that various changes may be made therein without departing from the spirit of the invention which is defined by the following claims.

I claim:

1. A safety belt for confining a bed patient to relatively free movement within limits, said safety belt comprising:
    (a) a pair of laterally offset, flexible, securing straps; and
    (b) a pair of cross straps transversely intersecting intermediate portions of said securing straps and transversely crossing each other, one said cross strap being attached at its opposite ends to two of the similarly facing sides of each securing strap and the other of said cross straps attached at its opposite ends to the other sides of said securing straps.

2. A safety belt according to claim 1 wherein said securing straps have connector means to aid in the securing of said straps.

3. A safety roll belt for attachment to a bed and to a bed patient for confining said patient to relatively free movement within limits, said safety belt, in its operable position, comprising:

(a) a first securing strap attached near a first one of its ends to a side of said bed and extending therefrom laterally upon the bed, beneath the patient to the opposite one of his sides and at least partially surrounding said patient;

(b) a second securing strap attached near a first one of its ends to the opposite side of said bed, offset from said first securing strap and extending therefrom laterally upon the bed, beneath the patient to the other side of the patient and at least partially surrounding said patient, the second end of said second strap extending into connection with the second end of said first securing strap; and (c) a pair of cross straps near the lateral center of said bed, an upper one of said cross straps being above, transversely intersecting and attached at each of its ends to a different one of said securing straps, and a lower one of said cross straps being transverse of said upper cross strap and below, transversely intersecting and attached at each of its opposite ends to a different one of said securing straps, said upper cross strap being attached to said securing straps at regions of the securing straps which are nearer the second ends of said securing straps than the regions at which the lower cross strap is attached to said securing straps.

4. A safety belt according to claim 3 wherein a pad is attached to said safety belt above said cross strap.

5. A safety belt according to claim 4 wherein said pad is provided with slots and wherein said securing straps extend from their regions of attachment to said upper cross strap through a different one of said slots into attachment with each other at their second ends.

6. A safety roll belt according to claim 3 wherein a buckle is provided on each of said securing straps near their first ends and a third buckle is provided on one of said securing straps near its second end.

7. A safety roll belt according to claim 3 wherein the distance between the regions of attachment for each strap is substantially in the range of seven inches to fifteen inches for confining the human body to desired limits of roll from the supine position.

* * * * *